United States Patent [19]

Bohn et al.

[11] Patent Number: 6,162,420
[45] Date of Patent: Dec. 19, 2000

[54] USE OF GLYCERYL TRIACETATE FOR TREATING ONYCHOMYCOSES

[75] Inventors: Manfred Bohn, Hofheim; Karl Theodor Kraemer, Langen; Astrid Markus, Liederbach, all of Germany

[73] Assignee: Hoechst Aktiengesellschaft, Frankfurt am Main, Germany

[21] Appl. No.: 08/776,101

[22] PCT Filed: May 3, 1996

[86] PCT No.: PCT/EP96/01855

§ 371 Date: Jan. 11, 1999

§ 102(e) Date: Jan. 11, 1999

[87] PCT Pub. No.: WO96/36311

PCT Pub. Date: Nov. 21, 1996

[30] Foreign Application Priority Data

May 18, 1993 [DE] Germany .................. 195 18 262

[51] Int. Cl.[7] .................. A61K 7/04; A61K 7/00; A61K 9/14; A01N 25/00
[52] U.S. Cl. .................. 424/61; 424/401; 424/405; 424/487; 514/345; 514/506
[58] Field of Search .................. 424/401, 487, 424/61, 405; 514/345, 506

[56] References Cited

U.S. PATENT DOCUMENTS

| 4,957,730 | 9/1990 | Bohn et al. |
| 5,066,484 | 11/1991 | Castroglovanni et al. ......... 424/61 |
| 5,120,530 | 6/1992 | Ferro et al. |
| 5,264,206 | 11/1993 | Bohn et al. ......... 424/61 |
| 5,346,692 | 9/1994 | Wohlrab et al. |
| 5,603,939 | 2/1997 | Ser ......... 424/401 |
| 5,683,681 | 11/1997 | Ramin et al. ......... 424/61 |

FOREIGN PATENT DOCUMENTS 202098 10/1990 Hungary .

OTHER PUBLICATIONS

Martindale The Extra Pharmacopoeia 30th Ed., London The Pharmaceutical Press 1993, pp. 332, 1609.

Montana, et al., Cutis, 53:313–316 (1994), "A Double-–Blind, Vehicle–Controlled Study of the Safety and Efficacy of Fungoid Tincture® in Patients with Distal Subungual Onychmycosis of the Toes".

*Primary Examiner*—Shelley A. Dodson
*Assistant Examiner*—Marina Lamm
*Attorney, Agent, or Firm*—Finnegan, Henderson, Farabow, Garrett & Dunner, L.L.P.

[57] ABSTRACT

A nail varnish comprising glyceryl triacetate as an active compound and a water-insoluble film-forming agent is suitable for treatment of onychomycoses. If appropriate, the nail varnish can also additionally comprise antimycotic 1-hydroxy-2-pyridone derivatives.

21 Claims, No Drawings

USE OF GLYCERYL TRIACETATE FOR TREATING ONYCHOMYCOSES

This application is A 371 of PCT/EP96/01855 May 3, 1996.

DESCRIPTION

Fungal diseases of the nails (onychomycoses) belong to the infectious diseases which it has not been possible to treat satisfactorily to date. Although they progress largely painlessly for the patient, the permanent presence of a focus of infection renders treatment absolutely essential. In addition to circulatory disturbances and traumas, possibly predisposing factors for nail fungus infections are also immune defence deficiencies and certain metabolic disturbances (diabetes mellitus). Toenails are preferentially infected, the nails of the big and little toe chiefly being affected.

Analysis of the pathogen spectrum shows that onychomycoses are primarily caused by dermatophytes (for example *Trichophyton rubrum*), but also by yeasts (for example *Candida albicans*) or molds (for example *Scopulariopsis brevicaulis*). Apart from the white, superficial onychomycosis, the majority of infections take place below the body of the nail, in the nail bed or in the region of the matrix. Systemic, local or combined forms of treatment are considered, depending on the clinical appearance and the severity of the infection. Local treatment of the affected nail is the type of treatment which is gentlest for the patient and has the fewest side effects.

One known treatment form is an antimycotic preparation in the form of a nail varnish which comprises at least one antimycotic substance and at least one water-insoluble film-forming agent (EP 0 389 778). The low lateral diffusion in the nail of the antimycotic substances employed has proved to be a disadvantage of this type of formulation, so that only very incomplete effective treatment of the infected nail matrix and the areas of the nail bed lying under the nail wall is possible. Glyceryl triacetate (1,2,3-propanetriyl triacetate; $C_9H_{14}O_6$) is primarily used as a plasticizer for varnish formulations and for this purpose is also contained in a formulation according to EP 0 389 778. Glyceryl triacetate furthermore has fungistatic properties and is therefore occasionally used, especially in the USA, for treatment of superficial skin fungal diseases, but not for onychomycoses (Martindale "The Extra Pharmacopoeia", 30th Edition 1993; Roche Lexikon Medizin [Roche Dictionary of Medicine] 3rd Edition, 1993)

It has now been found that glyceryl triacetate is outstandingly suitable for treatment of onychomycoses because it shows good lateral diffusion through the nail and therefore allows treatment and prophylaxis of the nail matrix infected by dermatophytes and of the areas of the nail bed lying under the nail wall.

The invention therefore relates to the use of glyceryl triacetate for the preparation of a medicament for treatment and prophylaxis of onychomycoses.

A thorough cure can be achieved with the medicament according to the invention, especially in treatments of mycoses of the nail matrix, the nail usually growing again without deformation because growth of the dermatophytes in the nail root is prevented. In view of the poor treatment results to date, this is an extremely important finding.

The medicament according to the invention is also suitable for prophylactic use against nail mycoses, a sufficiently high depot of active compound being achieve in the nail, so that no outbreak of a nail disease caused by fungi occurs in the event of fungal contamination. The content of glyceryl triacetate in the medicament according to the invention is in general 0.1 to 25% by weight (wt. %), preferably 2 to 10 wt. %. The minimum content of glyceryl triacetate in the medicament is at least 0.1 to 1 wt. %; the medicament used for prophylaxis comprises less than 2 and advantageously at least 1 wt. % of glyceryl triacetate.

The invention furthermore relates to an antimycotic nail varnish comprising glyceryl triacetate and a water-insoluble film-forming agent.

The nail varnish according to the invention, i.e. the formulation comprising solvents, in general comprises glyceryl triacetate in an amount of 1 to 25 wt. %, preferably 2 to 10 wt. %, based on the amount of volatile and non-volatile constituents. The content of glyceryl triacetate in the medicinal nail varnishes, i.e. those for treatment, is usually 2 wt. %; the nail varnishes used for prophylaxis usually comprise less than 2 wt. % and advantageously at least 1 wt. % of glyceryl triacetate. The nail varnishes according to the invention in general comprise glyceryl triacetate in an amount of 6 to 80 wt. %, preferably 10 to 70 wt. % and in particular 15 to 60 wt. %, in each case based on the amount of non-volatile constituents, i.e. the sum of the film-forming agents, and any pigments, plasticizers and other non-volatile additives which may be present.

In addition to the glyceryl triacetate dissolved in a solvent or solvent mixture, the nail varnishes according to the invention also comprise, as necessary constituents, one or more film-forming agents which form a water-insoluble film on the nail after the formulation has dried.

Suitable water-insoluble film-forming agents are, for example, substances based on cellulose nitrate or physiologically acceptable polymers such as are customary in cosmetics, preferably as a mixture with cellulose nitrate. Examples which may be mentioned are polyvinyl acetate and partly hydrolyzed polyvinyl acetate, copolymers of vinyl acetate on the one hand and acrylic acid or crotonic acid or a maleic acid monoalkyl ester on the other hand, ternary copolymers of vinyl acetate on the one hand and crotonic acid and vinyl neododecanoate, or crotonic acid and vinyl propionate on the other hand, copolymers of methyl vinyl ether and a maleic acid monoalkyl ester, in particular maleic acid monobutyl ester, copolymers of a fatty acid vinyl ester and acrylic acid or methacrylic acid, copolymers of N-vinylpyrrolidone, methacrylic acid and a methacrylic acid alkyl ester, copolymers of acrylic acid and methacrylic acid or an acrylic acid alkyl ester or methacrylic acid alkyl ester, in particular with a content of quaternary ammonium groups, or polymers, copolymers or mixtures comprising ethyl acrylate, methyl methacrylate or trimethylammonioethyl methacrylate chloride, or polyvinyl acetals and polyvinyl butyrals, alkyl-substituted poly-N-vinylpyrrolidones, alkyl esters from copolymers of olefins and maleic anhydride and reaction products of colophony with acrylic acid. In the esters, the alkyl radicals are usually short-chain and usually have not more than four carbon atoms.

Possible physiologically acceptable solvents are substances such as hydrocarbons, halogenated hydrocarbons, alcohols, ethers, ketones and esters which are customary in cosmetics, in particular acetic acid esters of monohydric alcohols, such as ethyl and butyl acetate, if appropriate mixed with aromatic hydrocarbons, such as toluene, and/or alcohols, such as ethanol or isopropanol. The combination of the solvents is known to be of decisive importance for the drying time, brushability and other important properties of the varnish or of the varnish film. The solvent system preferably comprises an optimum mixture of low-boiling agents (=solvents having a boiling point up to 100° C.) and medium-boiling agents (=solvents having a boiling point up to 200° C.).

The nail varnishes according to the invention can furthermore comprise additives customary in cosmetics, such as plasticizers based on phthalate or camphor, dyestuffs or colored pigments, pearly luster agents, sedimentation retardants, suflonamide resins, silicates, odiferous substances, wetting agents, such as sodium dioctyl sulfosuccinate, lanolin derivatives, light stabilizers, such as 2-hydroxy-4-methoxybenzophenone, antibacterial substances and substances having a keratolytic and/or keratoplastic action, such as ammonium sulfite, esters and salts of thioglycolic acid, urea, allantoin, enzymes and salicylic acid.

Colored or pigmented nail varnishes have the advantage, for example, that the formulation according to the invention can be adapted to suit the aesthetic sensibilities of the patient.

The medicament according to the invention and the nail varnish are prepared in the customary manner by bringing the individual components together and further processing—if necessary—appropriate for the particular formulation.

The invention furthermore relates to an antimycotic nail varnish comprising a) glyceryl triacetate, b) a 1-hydroxy-2-pyridone of the formula I in which $R^1$, $R^2$ and $R^3$, which are identical or different, are hydrogen atom or alkyl having 1–4 carbon atoms and $R^4$ is a saturated hydrocarbon radical having 6 to 9 carbon atoms or a radical of the formula II in which X is S or O, Y is a hydrogen atom or up to 2 halogen atoms, such as chlorine and/or bromine, Z is a single bond or the divalent radicals O, S or —$CR^2$— (R=H or $C_1$–$C_4$-alkyl) or other divalent radicals having 2–10 carbon atoms and optionally O and/or S atoms linked in the form of a chain, where—if the radicals contain 2 or more O and/or S atoms—the latter must be separated from one another by at least 2 carbon atoms, and where 2 adjacent carbon atoms can also be linked to one another by a double bond and the free valencies of the carbon atoms are saturated by H and/or $C_1$–$C_4$-alkyl groups, and Ar is an aromatic ring system having up to two rings, which can be substituted by up to three radicals from the group consisting of fluorine, chlorine, bromine, methoxy, $C_1$–$C_4$-alkyl, trifluoromethyl and trifluoromethoxy, and c) a water-insoluble filme-forming agent.

The term "saturated" here describes those radicals which contain no aliphatic multiple bonds, i.e. no ethylenic or acetylenic bonds.

In the radicals "Z", the carbon chain members are preferably $CH_2$ groups. If the $CH_2$ groups are substituted by $C_1$–$C_4$-alkyl groups, preferred substituents are $CH_3$ and $C_2H_5$. Examples of radicals "Z" are: —O—, —S—, —$CH_2$—, —$(CH_2)_m$— (m=2–10), —$C(CH_3)_2$—, —$CH_2O$—, —$OCH_2$—, —$CH_2S$—, —$SCH_2$—, —$SCH(C_2H_5)$—, —CH=CH—$CH_2O$—, —O—$CH_2$—CH=CH—$CH_2O$—, —$OCH_2$—$CH_2O$—, —$OCH_2$—$CH_2CH_2O$—, —$SCH_2CH_2CH_2S$—, —$SCH_2CH_2CH_2CH_2O$—, —$SCH_2CH_2OCH_2CH_2O$—, —$SCH_2CH_2OCH_2CH_2O$ —$CH_2CH_2S$— or —S—$CH_2$—$C(CH_3)_2$—$CH_2$—S—.

The radical "S" is a sulfur atom and the radical "O" is an oxygen atom. The term "Ar" is phenyl and fused systems such as naphthyl, tetrahydronaphthyl and indenyl, as well as isolated systems, such as those which are derived from biphenyl, diphenylalkanes, diphenyl ethers and diphenyl thioethers.

In the formula I, the hydrocarbon radical $R^4$ is an alkyl or cyclohexyl radical, which can also be bonded to the pyridone ring via a methylene or ethylene group or can contain an endomethyl group. $R^4$ can also be an aromatic radical, which is, however, preferably bonded to the pyridone radical via at least one aliphatic carbon atom.

Important representatives of the class of compound characterized by the formula I are:

6-[4-(4-chloro-phenoxy)-phenoxymethyl]-1-hydroxy-4-methyl-2-pyridone, 6-[4-(2,4-dichloro-phenoxy)-phenoxymethyl]-1-hydroxy-4-methyl-2-pyridone, 6-(biphenylyl-4-oxy-methyl)-1-hydroxy-4-methyl-2-pyridone, 6-(4-benzyl-phenoxymethyl)-1-hydroxy-4-methyl-2-pyridone, 6-[4-(2,4-dichlorobenzyloxy)-phenoxy-methyl]-1-hydroxy-4-methyl-2-pyridone, 6-[4-(4-chloro-phenoxy)-phenoxymethyl]-1-hydroxy-3,4-dimethyl-2-pyridone, 6-[4-(2,4-dichloro-benzyl)-phenoxymethyl]-1-hydroxy-3,4-dimethyl-2-pyridone, 6-[4-(cinnamyloxy)-phenoxymethyl]-1-hydroxy-4-methyl-2-pyridone, 1-hydroxy-4-methyl-6-[4-(4-trifluoromethyl-phenoxy)-phenoxymethyl]-2-pyridone, 1-hydroxy-4-methyl-6-cyclohexyl-2-pyridone, 1-hydroxy-4-methyl-6-(2,4,4-trimethylpentyl)-2-pyridone, 1-hydroxy-4-methyl-6-n-hexyl-, -6-iso-hexyl-, -6-n-heptyl- or -6-iso-heptyl-2-pyridone, 1-hydroxy-4-methyl-6-octyl- or -6-iso-octyl-2-pyridone, in particular 1-hydroxy-4-methyl-6-cyclohexyl-methyl- or -6-cyclohexylethyl-2-pyridone, where the cyclohexyl radical in each case can also carry a methyl radical, 1-hydroxy-4-methyl-6-(2-bicyclo[2.2.1]heptyl)-2-pyrodine, 1-hydroxy-3,4-dimethyl-6-benzyl- or -6-di-methylbenzyl-2-pyridone or 1-hydroxy-4-methyl-6-(β-phenyl-ethyl)-2-pyridone.

The content of water-insoluble film-forming agents, glyceryl triacetate, solvents and other additives corresponds to that of the abovementioned nail varnish comprising glyceryl triacetate and a water-insoluble film-forming agent.

The content of the compound of the formula I in the nail varnish according to the invention depends on the structure of each compound of the formula I and therefore on the release thereof from the varnish film, its penetration properties in the nail and its antimicrobial properties.

The nail varnish according to the invention, i.e. the use form comprising solvents, in general comprises the compound of the formula I in an amount of 0.5 to 20, preferably 2 to 15 wt. %, based on the amount of volatile and non-volatile constituents. The content in the medicinal nail varnishes, i.e. those for treatment, is usually 4 wt. %; the nail varnishes used for prophylaxis usually comprise less than 4 and advantageously at least 1 wt. % of the compound of the formula I. The nail varnishes according to the invention in general comprise the compound of the formula I in an amount of 2 to 80 percent by weight, preferably 10 to 60 wt. % and in particular 20 to 40 wt. %, in each case based on the amount of non-volatile constituents, i.e. the sum of film-forming agents, glyceryl triacetate, and any pigments, plasticizers and other non-volatile additives which may be present.

The nail varnishes comprising a compound of the formula I are prepared by bringing the individual components together and further processing—if necessary—appropriate for the particular type of formulation (EP 0 226 984). Some of these diverse possible formulation forms are described by way of example in the embodiment examples.

EXAMPLE 1

A formulation according to the invention has the following composition:

| | |
|---|---|
| Glyceryl triacetate | 6.0 wt. % |
| Isopropyl alcohol | 47.0 wt. % |
| Ethyl acetate | 32.0 wt. % |
| Copolymer of methyl vinyl ether and maleic acid monobutyl ester | 15.0 wt. % |

The nail varnish is prepared by dissolving the various components in the solvents.

EXAMPLE 2

A formulation according to the invention has the following composition:

| | |
|---|---|
| Glyceryl triacetate | 2.5 wt. % |
| 1-Hydroxy-4-methyl-6-cyclohexyl-2-pyridone | 5.0 wt. % |
| Isopropyl alcohol | 46.5 wt. % |
| Ethyl acetate | 36.0 wt. % |
| Copolymer of methyl vinyl ether and maleic acid monobutyl ester | 10.0 wt. % |

EXAMPLE 3

A formulation according to the invention has the following composition:

| | |
|---|---|
| Glyceryl triacetate | 2.5 wt. % |
| 1-Hydroxy-4-methyl-6-(2,4,4-trimethylpentyl) 2-pyridone | 2.5 wt. % |
| Isopropyl alcohol | 47.5 wt. % |
| Ethyl acetate | 40.0 wt. % |
| Copolymer of methyl vinyl ether and maleic acid monobutyl ester | 7.5 wt. % |

EXAMPLE 4

Testing of Activity

The experiments to demonstrate the lateral penetration of glyceryl triacetate through keratin material is carried out as follows using the formulations mentioned in Examples 1 to 3:

From the horny part of a cow horn, platelets approximately 0.5 mm thick and 1.5×3 cm in size are dissected and are treated daily on one half of one side on 5 successive days with the particular formulation containing the active compound. The platelets are then fixed in a humid chamber on metal cylinders about 0.5 cm above an aqueous agar surface with the sides treated on one half facing downwards. The entire side of the horn facing upwards is inoculated several times in point form with a microconidia suspension of Trichophyton mentagrophytes. The colony formation is then observed at 28° C. for 10 days.

Result:

The 5 pretreatments over half of the reverse side of the horn with the formulations according to the invention of Example 1 to 3 completely prevented germination of the fungal spores over the entire upper side. Even the inoculation points were no longer visible macroscopically over the entire upper side after a few days. The action of the formulation according to the invention therefore extends laterally from the treatment region over the entire surface of the piece of horn.

The control platelets without treatment with the formulation according to the invention show complete growth on the horn surface after inoculation.

A control platelet treated with a formulation comprising the formulation according to Example 2 but without glyceryl triacetate shows no growth directly above the treated side of the horn, while growth of the fungus is to be observed on the other half of the platelet (not treated with the formulation).

What is claimed is:

1. A nail varnish composition for prophylaxis or treatment of an onychomychosis, comprising glyceryl triacetate, a water-insoluble film-forming agent, and a 1-hydroxy-2-pyridone of the formula I

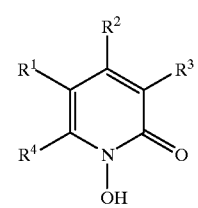

(I)

in which $R^1$, $R^2$ and $R^3$, which are identical or different, are hydrogen atom or alkyl having 1–4 carbon atoms and $R^4$ is a saturated hydrocarbon radical having 6 to 9 carbon atoms or a radical of the formula II

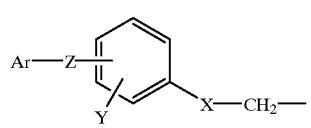

(II)

in which

X is S or O,

Y is a hydrogen atom or up to 2 halogen atoms which are the same or different,

Z is a single bond or the divalent radicals O, S or —CR$_2$—(R=H or $C_1$–$C_4$-alkyl) or other divalent radicals having 2–10 carbon atoms linked in the form of a chain, wherein said chain optionally further comprises at least one O atom, at least one S atom, or a combination thereof, where—if said other divalent radicals contain two or more O atoms, S atoms, or a combination thereof—said O atoms and S atoms must be separated from one another by at least two carbon atoms, and where two adjacent carbon atoms are optionally linked to one another by a double bond and the free valencies of the carbon atoms are saturated by H atoms, $C_1-C_4$-alkyl groups, or a combination of H atoms and $C_1-C_4$-alkyl groups, and Ar is an aromatic ring system having up to two rings, which can be substituted by up to three radicals which are the same or different and are selected from the group consisting of fluorine, chlorine, bromine, methoxy, $C_1-C_4$-alkyl, trifluoromethyl, and trifluoromethoxy.

2. A nail varnish composition as claimed in claim 1, in which Ar, in the 1-hydroxy-2-pyridone of the formula I, is a bicyclic system derived from biphenyl.

3. A nail varnish composition as claimed in claim 1, wherein the 1-hidroxy-2-pyridone of the formula I contains a cyclohexyl radical in the position $R^4$.

4. A nail varnish composition as claimed in claim 1, wherein the 1-hidroxy-2-pyridone of the formula I contains an octyl radical of the formula —$CH_2$—$CH(CH_3)$—$CH_2$—$C(CH_3)_3$ in the position $R^4$.

5. A nail varnish composition as claimed in claim 1, wherein the 1-hydroxy-2-pyridone of the formula I is 6-(4-(4-chloro-phenoxy)-phenoxymethyl)-1-hydroxy-4-methyl-2-pyridone, 1-hydroxy-4-methyl-6-cyclohexyl-2-pyridone, 1-hydroxy-4-methyl-6-(2,4,4-trimethylpentyl)-2-pyridone, or a combination of any two or more of the foregoing.

6. A nail varnish composition as claimed in one of claims 1 to 5, comprising the 1-hydroxy-2-pyridone of the formula I in an amount of 2 to 80% by weight, based on the amount of non-volatile constituents.

7. A nail varnish composition as claimed in claim 1, in which Y, in the 1-hydroxy-2-pyridone of the formula I, is chlorine or bromine.

8. A nail varnish composition as claimed in claim 2, in which Ar, in the 1-hydroxy-2-pyridone of the formula I, is a diphenylalkane or a diphenyl ether.

9. A nail varnish composition as claimed in claim 6, which comprises the 1-hydroxy-2-pyridone of the formula I in an amount of 10 to 60% by weight, based on the amount of non-volatile constituents.

10. A nail varnish composition as claimed in claim 9, which comprises the 1-hydroxy-2-pyridone of the formula I in an amount of 20 to 40% by weight, based on the amount of non-volatile constituents.

11. A method for preparing a medicament for treatment or prophylaxis of an onychomycosis, comprising:

combining glyceryl triacetate in a concentration effective for said treatment or prophylaxis of an onychomycosis, with a water-insoluble film-forming agent, and at least one 1-hydroxy-2-pyridone of the formula I

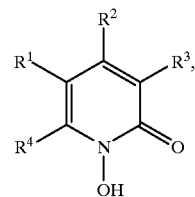

in which $R^1$, $R^2$ and $R^3$, which are identical or different, are hydrogen atom or alkyl having 1–4 carbon atoms and $R^4$ is a saturated hydrocarbon radical having 6 to 9 carbon atoms or a radical of the formula II

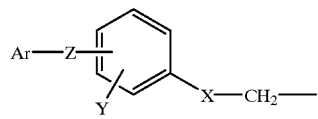

in which

X is S or O,

Y is a hydrogen atom or up to 2 halogen atoms which are the same or different,

Z is a single bond or the divalent radicals O, S or —$CR_2$—(R=H or $C_1-C_4$-alkyl) or other divalent radicals having 2 to 10 carbon atoms linked in the form of a chain, wherein said chain optionally further comprises at least one O atom, at least one S atom, or a combination thereof, where—if said other divalent radicals contain two or more O atoms, S atoms, or a combination thereof—said O atoms and S atoms must be separated from one another by at least two carbon atoms, and where two adjacent carbon atoms are optionally linked to one another by a double bond and the free valencies of the carbon atoms are saturated by H atoms, $C_1-C_4$-alkyl groups, or a combination of H atoms and $C_1-C_4$-alkyl groups, and Ar is an aromatic ring system having up to two rings, which can be substituted by up to three radicals which are the same or different and are selected from the group consisting of fluorine, chlorine, bromine, methoxy, $C_1-C_4$-alkyl, tri-fluoromethyl, and trifluoromethoxy, to produce said medicament.

12. A method for treating or preventing an onychomycosis in a human or animal patient in need of such treating or preventing, comprising the step of administering to a nail of said patient a composition comprising an amount of glyceryl triacetate effective for said treating or preventing, a water-insoluble film-forming agent, and at least one 1-hydroxy-2-pyridone of the formula I

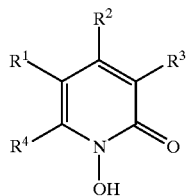
(I)

in which $R^1$, $R^2$ and $R^3$, which are identical or different, are hydrogen atom or alkyl having 1–4 carbon atoms and $R^4$ is a saturated hydrocarbon radical having 6 to 9 carbon atoms or a radical of the formula II

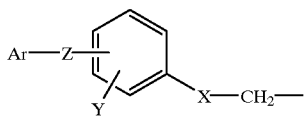
(II)

in which
X is S or O,
Y is a hydrogen atom or up to 2 halogen atoms which are the same or different,
Z is a single bond or the divalent radicals O, S or —CR$_2$—(R=H or $C_1$–$C_4$-alkyl) or other divalent radicals having 2 to 10 carbon atoms linked in the form of a chain,
  wherein said chain optionally further comprises at least one O atom, at least one S atom, or a combination thereof, where—if said other divalent radicals contain two or more O atoms, S atoms, or a combination thereof—said O atoms and S atoms must be separated from one another by at least two carbon atoms, and
  where two adjacent carbon atoms are optionally linked to one another by a double bond and the free valencies of the carbon atoms are saturated by H atoms, $C_1$–$C_4$-alkyl groups, or a combination of H atoms and $C_1$–$C_4$-alkyl groups, and Ar is an aromatic ring system having up to two rings, which can be substituted by up to three radicals which are the same or different and are selected from the group consisting of fluorine, chlorine, bromine, methoxy, $C_1$–$C_4$-alkyl, tri-fluoromethyl, and trifluoromethoxy.

13. The method of claim 12, in which Y, in the 1-hydroxy-2-pyridone of the formula I, is chlorine or bromine.

14. The method of claim 12, in which Ar, in the 1-hydroxy-2-pyridone of the formula I, is a bicyclic system derived from biphenyl.

15. The method of claim 14, in which Ar, in the 1-hydroxy-2-pyridone of the formula I, is a diphenylalkane or a diphenyl ether.

16. The method of claim 12, in which the 1-hydroxy-2-pyridone of the formula I contains a cyclohexyl radical in the position $R^4$.

17. The method of claim 12, in which the 1-hydroxy-2-pyridone of the formula I contains an octyl radical of the formula —CH$_2$—CH(CH$_3$)—CH$_2$—C(CH$_3$)$_3$ in the position $R^4$.

18. The method of claim 12, wherein the 1-hydroxy-2-pyridone of the formula I is 6-(4-(4-chloro-phenoxy)-phenoxymethyl)-1-hydroxy-4-methyl-2-pyridone, 1-hydroxy-4-methyl-6-cyclohexyl-2-pyridone, 1-hydroxy-4-methyl-6-(2,4,4-trimethylpentyl)-2-pyridone, or a combination of any two or more of the foregoing.

19. The method of claim 12, wherein the 1-hydroxy-2-pyridone of the formula I is present in an amount of 2 to 80% by weight, based on the amount of non-volatile constituents.

20. The method of claim 19, wherein the 1-hydroxy-2-pyridone of formula I is present in an amount 10 to 60% by weight, based on the amount of non-volatile constituents.

21. The method of claim 20, wherein the 1-hydroxy-2-pyridone of formula I is present in an amount 20 to 40% by weight, based on the amount of non-volatile constituents.

* * * * *

UNITED STATES PATENT AND TRADEMARK OFFICE
CERTIFICATE OF CORRECTION

PATENT NO.     : 6,162,420
DATED          : December 19, 2000
INVENTOR(S)    : Manfred Bohn et al.

It is certified that error appears in the above-identified patent and that said Letters Patent is hereby corrected as shown below:

<u>Column 7,</u>
Lines 24 and 27, "1-hidroxy-2-pyridone" should read -- 1-hydroxy-2-pyridone --.

Signed and Sealed this

Twenty-third Day of December, 2003

JAMES E. ROGAN
*Director of the United States Patent and Trademark Office*